US008000769B2

(12) United States Patent
Yu et al.

(10) Patent No.: US 8,000,769 B2
(45) Date of Patent: Aug. 16, 2011

(54) METHODS FOR FAT QUANTIFICATION WITH CORRECTION FOR NOISE BIAS

(75) Inventors: Huanzhou Yu, Mountain View, CA (US); Scott Brian Reeder, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 717 days.

(21) Appl. No.: 11/923,369

(22) Filed: Oct. 24, 2007

(65) Prior Publication Data

US 2009/0112081 A1 Apr. 30, 2009

(51) Int. Cl.
*A61B 5/055* (2006.01)
(52) U.S. Cl. ........................................ 600/410; 600/411
(58) Field of Classification Search .................. 600/407, 600/410
See application file for complete search history.

(56) References Cited

U.S. PATENT DOCUMENTS

| 6,147,492 A | 11/2000 | Zhang et al. |
| 6,856,134 B1 | 2/2005 | Reeder et al. |

OTHER PUBLICATIONS

Zhang, X., Measurement of Fat/Water Ratios in Rat Liver Using 3D Three-Point Dixon MRI, Magnetic Resonance in Medicine, 2004, 51:697-702.

Liu C-Y et al; Fat Quantification With IDEAL Gradient Echo Imaging: Correction of Bias From T1 and Noise; Magnetic Resonance in Medicine, Academic Press, Duluth MN. vol. 58, Jul. 27, 2007; pp. 354-364.

Reeder S B et al; Multicoil Dixon Chemical Species Separation With an Iterative least-Squares Estimation Method; Magnetic Resonance in Medicine, Academic Press, Duluth MN. vol. 51, No. 1; Jan. 1, 2004; pp. 35-46.

Yu H et al; Single Acquisition Water-Fat Separation: feasibility Study For Dynamic Imaging: Magnetic Resonance in Medicine, Academic Press, Duluth MN. vol. 55, 2006, pp. 413-422.

Hussain HK et al; Hepatic Fat Fraction: MR Imaging for Quantitative Measurement and Display-Early Experience; Radiology; vol. 237, 2005, pp. 1048-1055.

*Primary Examiner* — Long V Le
*Assistant Examiner* — Nicholas L Evoy
(74) *Attorney, Agent, or Firm* — Quarles & Brady LLP

(57) ABSTRACT

Methods are disclosed for calculating a fat fraction corrected for noise bias of one or more voxels of interest using a magnetic resonance imaging (MRI) system. A plurality of image data sets are obtained each corresponding to NMR k-space data acquired using a pulse sequence with an individual associated echo time $t_n$. A system of linear equations is formed relating image signal values to a desired decomposed calculated data vector having a component such as a water and fat combination having zero mean noise, or having a real fat component and a real water component. A fat fraction is calculated from at least one component of the decomposed calculated data vector. In another embodiment, the system of linear equations is normalized and can directly estimate a fat fraction or a water fraction having reduced noise bias.

11 Claims, 4 Drawing Sheets

METHODS FOR FAT QUANTIFICATION WITH CORRECTION FOR NOISE BIAS

FIELD OF THE INVENTION

The field of the invention is magnetic resonance imaging ("MRI") methods and systems. More particularly, the invention relates to methods for fat quantification, such as determining a fat fraction, with correction for noise bias.

BACKGROUND OF THE INVENTION

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, Mz, may be rotated, or "tipped", into the x-y plane to produce a net transverse magnetic moment $M_t$. A signal is emitted by the excited spins after the excitation signal $B_1$ is terminated, this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

In an magnetic resonance imaging sequence, a uniform magnetic field $B_0$ is applied to an imaged object along the z axis of a Cartesian coordinate system. The effect of the magnetic field $B_0$ is to align the object's nuclear spins along the z axis. In this field, the nuclei resonate at their Larmor frequencies according to $\omega=\gamma B_0$, where $\omega$ is the Larmor frequency, and $\gamma$ is the gyromagnetic ratio which is a property of the particular nucleus. The nuclei respond to RF pulses at this frequency by tipping their longitudinal magnetization into the transverse, x-y plane. Hydrogen (protons) in water, because of its relative abundance in biological tissue and the properties of its proton nuclei, is the imaging species of choice for most MRI applications. The value of the gyromagnetic ratio $\gamma$ for protons in water is 4.26 kHz/Gauss and therefore in a 1.5 Tesla polarizing magnetic field $B_0$, the resonant or Larmor frequency of water protons is approximately 63.9 MHz.

Materials other than water, principally fat, are also to be found in biological tissue and have different gyromagnetic ratios. The Larmor frequency of protons in fat is approximately 210 Hz lower than that of protons in water in a 1.5 Tesla polarizing magnetic field $B_0$. The difference between the Larmor frequencies of such different isotopes or species of the same nucleus, namely protons, is termed chemical shift, reflecting the differing chemical environments of the two species.

In the well known slice selective RF pulse sequence, a slice selective magnetic field gradient $G_z$ is applied at the time of the RF pulse so that only the nuclei in a slice through the object in an x-y plane are excited. After the excitation of the nuclei, magnetic field gradients are applied along the x and y axes and an NMR signal is acquired. The readout gradient $G_x$ along the x axis causes the nuclei to precess at different resonant frequencies depending on their position along the x axis; that is, $G_x$ spatially encodes the precessing nuclei by frequency. But because water and fat spins resonate at different frequencies, even when they are in the same location, their locations in the reconstructed image will be shifted with respect to each other. This is particularly problematic on the boundaries of tissues or organs where this chemical shift can cause blurring or multiple edges.

There is a large body of work that has been developed to selectively suppress certain signals such as the signals from fat. Reliable and uniform fat suppression is essential for accurate diagnoses in many areas of MRI. This is particularly true for MRI applications using certain pulse sequences such as fast spin-echo (FSE), steady-state free precession (SSFP) and gradient echo (GRE) imaging, in which fat is bright in the resultant images and may obscure underling pathology. Although conventional fat saturation may be adequate for areas of the body with a relative homogeneous $B_0$ field, there are applications in which fat saturation routinely fails. This is particularly true for extremity imaging, off-isocenter imaging, large field of view (FOV) imaging, and challenging areas such as the brachial plexus and skull based, as well as many others. Short-TI inversion recovery (STIR) imaging provides uniform fat suppression, but at a cost of reduced signal-to-noise ratio (SNR) for the water image and mixed contrast that is dependent on $T_1$, (Bydder G M, Pennock J M, Steiner R E, Khenia S, Payne J A, Young I R, The Short T1 Inversion Recovery Sequence-An Approach To MR Imaging Of The Abdomen, Magn. Reson. Imaging 1985; 3(3):251-254). This latter disadvantage limits STIR imaging to $T_2$ weighted ($T_2W$) applications, such that current $T_1$ weighted ($T_1W$) applications rely solely on conventional fat-saturation methods. Another fat suppression technique is the use of spectral-spatial or water selective pulses; however, this method is also sensitive to field inhomogeneities, (Meyer C H, Pauly J M, Macovski A, Nishimura D G, Simultaneous Spatial And Spectral Selective Excitation, Magn. Reson. Med. 1990; 15(2):287-304).

Other techniques have also been developed to obtain separate water and/or fat images. For example, "In and Out of Phase" Imaging was first described by Dixon in 1984, and is used to exploit the difference in chemical shifts between water and fat in order to separate water and fat into separate images, Dixon W. Simple Proton Spectroscopic Imaging, Radiology 1984; 153:189-194. Glover et al. further refined this approach in 1991 with a 3 point method that accounts for magnetic field inhomogeneities created by susceptibility differences, Glover G H, Schneider E, Three-Point Dixon Technique For True Water/Fat Decomposition With B0 Inhomogeneity Correction, Magn. Reson. Med. 1991; 18(2):371-383; Glover G, Multipoint Dixon Technique For Water and Fat Proton and Susceptibility Imaging, Journal of Magnetic Resonance Imaging 1991; 1:521-530. Hardy et al first applied this method with FSE imaging by acquiring three images with the readout centered at the spin-echo for one image and symmetrically before and after the spin-echo in the subsequent two images, Hardy P A, Hinks R S, Tkach J A, Separation Of Fat And Water In Fast Spin-Echo MR Imaging With The Three-Point Dixon Technique, J. Magn. Reson. Imaging 1995; 5(2):181-195.

Also recently, a water-fat separation method known as IDEAL (Iterative Decomposition of water and fat with Echo Asymmetry and Least squares estimation) has been described by Reeder S, Pineda A, Wen Z, et al., in Iterative Decomposition of Water and Fat With Echo Asymmetry and Least-Squares Estimation (IDEAL): Application with Fast Spin-echo Imaging, Magn Reson Med 2005; 54(3);636-644. IDEAL is an SNR-efficient method that uses flexible echo spacings and when combined with optimized echo spacings can provide the best possible SNR performance.

In addition to separation of water and fat, the accurate quantification of fat, especially in the liver, is an increasingly important unmet need. Nonalcoholic fatty liver disease is a term that incorporates a spectrum of histologic findings ranging from simple steatosis (fatty infiltration) to fibrosis, cirrhosis and liver failure. Nonalcoholic steatohepatitis is an intermediate stage characterized by steatosis and hepatic cell inflammation. These liver changes can progress to cirrhosis and even death, such that it is desirable to be able to accurately measure fat in the liver in order to provide early treatment and prevent progression of the disease. Currently, the definitive diagnosis of nonalcoholic fatty liver disease is determined with a liver biopsy.

MRI is a non-invasive method that can also be used to detect fatty infiltration of the liver, although quantification of fat in the liver has been limited, due to limitations in estimation of water and fat signals, including the effects of image noise bias, as explained below.

Consider the signal model for a voxel containing water (W) and fat (F), with a chemical shift frequency of $\Delta f$, which depends on the magnitude of the magnetic field $B_0$ (e.g., −210 Hz at 1.5 T and −420 Hz at 3 T), acquired at an echo time of $t_n$:

$$s(t_n)=(We^{i\phi_W}+Fe^{i\phi_F} \cdot e^{i2\pi\Delta f \cdot t_n})e^{i2\pi\psi t_n} \quad \text{Equation 1}$$

where $\phi_W$ is the time-independent phase of water and $\phi_F$ is the time independent phase of fat, and these phases can be unequal to each other; $\psi$ is the local field inhomogeneity map (Hz); and W and F are real.

If a number N of images are acquired corresponding to different echo times $t_n$, then methods such as IDEAL can be used to provide an estimate of the field inhomogeneity map $\psi$, demodulate the effects of the field map from the signal and subsequently decompose the water and fat signals into different images, i.e., to provide estimates of a complex water component $\hat{W}=We^{i\phi_W}$, and a complex fat component, $\hat{F}=Fe^{i\phi_F}$.

There are several advantages to using the above signal model and allowing the phase of water and fat to be independent. The major advantage is that errors in the presumed chemical shift between water and fat (denoted by $\Delta f$) will manifest primarily as phase errors in these complex components $\hat{W}$ and $\hat{F}$, rather than as magnitude errors. For many applications, accurate estimation of the magnitude of water and fat signals is far more important. Therefore, although the phase angles could be set equal to one another, for estimation purposes, it is preferred that they be independent. Then, in order to calculate the fat fraction $\eta$, defined as:

$$\eta = \frac{F}{F+W}, \quad \text{Equation 2}$$

The magnitudes of complex quantities $\hat{W}$ and $\hat{F}$ are calculated (i.e. $|\hat{W}|$ and $|\hat{F}|$) and used to calculate the fat fraction according to:

$$\eta = \frac{|\hat{F}|}{|\hat{F}|+|\hat{W}|}. \quad \text{Equation 3}$$

SUMMARY OF THE INVENTION

One aspect of the present invention is the realization that the magnitude image data calculated from the decomposed complex water and fat image signals is not sufficient to provide an accurate calculation of fat fraction at a low SNR. Thus, while solving Equation 1 above provides estimates of the complex water and fat signals at a voxel, and the magnitudes of these complex water and fat signals can be calculated and used in Equation 3 to provide a reasonably accurate calculation of fat fraction when there is little noise, with greater amounts of noise, a bias will be introduced that should be considered when calculating true fat fraction. This bias is especially prevalent at low fat fractions and high fat fractions (low water fractions). In particular, the noise in complex MR images is Gaussian with zero mean, as shown in FIG. 1(a). However, most MR images are displayed as magnitude images. In areas with a high signal to noise ratio (SNR greater than approximately 3-5), the noise statistics are unaffected and remain Gaussian with zero mean. However in regions of low signal to noise ratio (SNR less than 3-5), the noise distribution is skewed and is in fact a Rician distribution having a biased, non-zero mean, such as is shown in FIG. 1(b) for magnitude image data that is calculated from the complex image signals. In such a case, if the magnitude image data is used to calculate the fat fraction, then the fat fraction will have bias, as illustrated in FIG. 2. Specifically, FIG. 2 shows the effect of the noise bias in a Monte Carlo simulation that uses magnitude data in the presence of zero mean Gaussian noise based on a SNR of 10 (ignoring the effects of $T_1$). Note that a calculated fat fraction is most inaccurate if it has a value near zero or a value near one. A positive bias of nearly 10% is seen when the true fat fraction is zero. Thus, measurement of low and high fat fractions will be biased if magnitude image fat data calculated from complex image signals is used to calculate the fat fraction. This is of great clinical relevance, because the detection of early steatosis is extremely important—it is the earliest biomarker of non-alcoholic fatty liver disease.

Noise bias can be reduced by adjusting the image parameters to increase the SNR of the image, but this is not always a practical solution and may require excessive signal averaging and/or unacceptable reductions in spatial resolution. Thus, a general object of the present invention is to provide ways to reduce or correct for the noise bias that occurs in low SNR images, particularly at low fat fractions. This noise bias correction is especially important in applications such as liver imaging where it is desirable to accurately quantify a fat fraction of the liver, although this also applies to fatty deposition in other tissues of interest including, but not limited to, skeletal muscle and adrenal glands.

One aspect of the invention is a correction for the noise bias using a phase constrained method. In one embodiment, unlike the signal model of Equation 1, where the phase of water and fat are assumed to be independent, a signal model is developed where the phase of water and fat are assumed to have a common, equal phase, i.e. Equation 1 is rewritten as follows:

$$s(t_n)=(W+Fe^{i2\pi\Delta f \cdot t_n})e^{i\phi}e^{i2\pi\psi \cdot t_n} \quad \text{Equation 4}$$

where $\phi$ is a common, time independent phase shift. This is a very reasonable assumption since the phase of water and fat within a voxel can be expected to be equal. Next, IDEAL can be modified to a phase constrained IDEAL decomposition algorithm, which is used to solve Equation 4 for W or F directly, i.e., to solve for a real water component and/or a real fat component, rather than solving Equation 1 for complex quantities $\hat{W}$ and $\hat{F}$. In this manner, there is no need to calculate the magnitude of a complex signal to calculate the fat fraction, such that calculating a fat fraction directly from the real water and fat components reduces its noise bias. As shown in FIG. 3, a Monte Carlo simulation demonstrates that the use of a phased constrained IDEAL decomposition completely removes the bias seen at low and high values of fat fraction.

Another aspect of the invention is a correction of the noise bias using a signal normalization method. In one embodiment of a signal normalization method, an in-phase image signal is acquired corresponding to when the water and the fat are in phase (aligned), and two or more other image data signals are acquired at different respective echo times. These other image data signals are then "normalized" by the corresponding in-phase signal, which occurs at:

$$t_n = \frac{k}{\Delta f} \quad \text{Equation 5}$$

where k is any integer, e.g. at a spin echo (k=0 in this case). It is a safe assumption that water and fat will be in phase at known specific times for most pulse sequences. For this in-phase signal, Equation 4 can then be written as:

$$s(k/\Delta f) = (W+F) e^{i\phi} e^{i 2\pi \psi k/\Delta f} \quad \text{Equation 6(a)}$$

since the phase of water and fat are equal, namely: $\phi_W = \phi_F = \phi$. Normalization of the image data signals occurs by dividing Equation 1 by Equation 6(a), which results in the following:

$$\eta_s(t_n) = (\eta_W e^{i\phi_{\eta W}} + \eta_F e^{i\phi_{\eta F}} e^{i2\pi\Delta f t_n}) e^{i2\pi\psi(t_n - k/\Delta f)} \quad \text{Equation 6(b)}$$

where $$\eta_W = \frac{W}{W+F}$$

is the water fraction and $$\eta_F = \frac{F}{W+F}$$

is the fat fraction, and $\eta_s(t_n)$ represents the normalized signal fraction acquired at $t_n$.

If the noise on the in-phase signal [Equation 6(a)] and the noise on the other acquired signal are both zero mean, then the noise on the normalized signal will also be zero mean. Therefore, subsequent estimates of water and fat fractions from Equation 6(b) should also have zero mean noise.

In Equation 6(b), it is not assumed that the phase of the water fraction and the fat fraction are equal for purposes of estimation. Known variables include $t_n$, $\Delta f$, and k. Measured variables include the normalized signal fractions $\eta_s(t_n)$, acquired at times $t_n$, and unknown variables to be estimated include $\hat{\eta}_W = \eta_W e^{i\phi_{\eta W}}$, $\hat{\eta}_F = \eta_F e^{i\phi_{\eta F}}$ and $\psi$.

Specifically, estimates of water and/or fat fraction can be made using a modification of the IDEAL method. If three or more image data sets are acquired, estimates of the field inhomogeneity map $\psi$ can be made and the phase shifts created by the field inhomogeneity map can be demodulated at each voxel to obtain:

$$\eta_s'(t_n) = (\eta_W e^{i\phi_{\eta W}} + \eta_F e^{i\phi_{\eta F}} e^{i2\pi\Delta f t_n}) = (\hat{\eta}_W + \hat{\eta}_F e^{i2\pi\Delta f t_n}) \quad \text{Equation 7}$$

Note that $\hat{\eta}_W$ and $\hat{\eta}_F$ are complex with independent phase. By obtaining image signal data corresponding to N different echo times, where N is greater than or equal to two, Equation 7 can be represented by a system of linear equations:

$$H_S = A \hat{H} \quad \text{Equation 8(a)}$$

where $$\hat{H} = [\hat{\eta}_W, \hat{\eta}_F] \quad \text{Equation 8(b)}$$

is a vector containing complex estimates of water and fat fractions; and $$H_S = [\eta_s'(t_1) \eta_s'(t_2) \ldots \eta_s'(t_N)] \quad \text{Equation 8(c)}$$

is an image signal vector for the n=1, ... N data points (not including the in-phase data point); and A represents the coefficient matrix, which takes into account the phase shifts due to different echo times:

$$A = \begin{vmatrix} 1 & e^{i2\pi\Delta f t_1} \\ 1 & e^{i2\pi\Delta f t_2} \\ \ldots & \ldots \\ 1 & e^{i2\pi\Delta f t_n} \end{vmatrix} \quad \text{Equation 8(d)}$$

The system of linear equations represented by Equation 8 can be solved using a least squares estimate such as a pseudo-inverse operation in order to obtain estimates for the fat fraction and water fraction as follows:

$$\hat{H} = (A^H A)^{-1} A^H H_S \quad \text{Equation 9}$$

where the superscript "H" represents the Hermitian transpose operator. In this manner, a complex fat fraction and a complex water fraction are directly obtained. At this stage the magnitudes of the water and fat fractions can be calculated. If the fat fraction is low, for example, taking the magnitude of the fat fraction will result in noise bias. However, because the sum of the water and fat fractions must be one, if the fat fraction is low, then the water fraction must be high and will be free of noise bias. The same principle applies for a low water fraction with a corresponding high fat fraction. Therefore, a magnitude discrimination method can be applied according to the following steps:

1. Calculate the magnitudes of the water and fat fractions, i.e., $|\hat{\eta}_W|$ and $|\hat{\eta}_F|$;
2. If $|\hat{\eta}_W| > |\hat{\eta}_F|$, then set $\hat{\eta}_F = 1 - |\hat{\eta}_W|$; otherwise use the calculated value of $|\hat{\eta}_F|$ as the estimate for the fat fraction, free of noise bias.

The above described embodiment requires the acquisition of at least three image data sets including one at an echo time where water and fat are in-phase. From these three images, the field inhomogeneity map is determined in the usual iterative manner according to the IDEAL method. The other two signals are then normalized by the in-phase image. Then the effects of the field map are demodulated from the normalized signals to produce Equation 7. Masking may be required for regions of very low signal (i.e., outside the body). The exact choice of echo times may require an analysis similar to that reported by Pineda et al. for water-fat separation. See Pineda A R, Reeder S B, Wen Z, Pelc N J., "Cramer-Rao Bounds for Three-point Decomposition of Water and Fat", at Magnetic Resonance in Medicine (September 2005; 54(3):625-35).

This method can be further simplified by assuming that the phase of water and fat fractions are equal in Equation 6(b), i.e. $\phi_{\eta W} = \phi_{\eta F} = \phi$, and realizing that the sum of the water fraction and the fat fraction must equal one, i.e.:

$$\eta_W + \eta_F = 1 \quad \text{Equation 10}$$

Thus Equation 6(b) can be written as follows:

$$\eta_S(t_n) = ((1-\eta_F)e^{i\phi} + \eta_F e^{i\phi} e^{i2\pi\Delta f t_n}) \cdot e^{i2\pi\psi(p_n - k/\Delta f)} \quad \text{Equation 11(a)}$$

$$\eta_S(t_n) = ((1-\eta_F) + \eta_F e^{i2\pi\Delta f t_n}) \cdot e^{i\phi} \cdot e^{i2\pi\psi(p_n - k/\Delta f)} \quad \text{Equation 11(b)}$$

$$\eta_S(t_n) = (1-\eta_F(1-e^{i2\pi\Delta f t_n})) \cdot e^{i\phi} \cdot e^{i2\pi\psi(p_n - k/\Delta f)} \quad \text{Equation 11(c)}$$

The outer phase shifts can be determined by methods similar to those described by Ma and Xiang, and demodulated in order to obtain:

$$\eta_S(t_n) = (1-\eta_F(1-e^{i2\pi\Delta f t_n})) \quad \text{Equation 12}$$

If two or more other image data sets are acquired, a least squares solution can be obtained through linear fitting of Equation 12 to determine an estimate for $\eta_F$. If only one other image is acquired in addition to the in-phase image, Equation 12 simplifies to a single equation:

$$\eta_F = \frac{1 - \eta_s(t_n)}{(1 - e^{i2\pi\Delta f t_n})} \quad \text{Equation 13}$$

Note that if the second image data is acquired out-of-phase, i.e., at $$t_n = \frac{2k+1}{2\Delta f} \quad \text{Equation 14}$$

then Equation 13 becomes:

$$\eta_F = \frac{1 - \eta_s\left(t_n = \frac{2k+1}{2\Delta f}\right)}{2} \quad \text{Equation 15}$$

Thus Equation 15 provides an estimate of the fat fraction free from the effects of noise bias, using only two image acquisitions, one acquired in-phase and the other acquired out-of-phase. Note that this modification would require phase unwrapping methods similar to those described recently by Ma or using the methods of Xiang if the second image is not exactly out-of-phase.

Another aspect of the invention is the calculation of the fat fraction using estimates of the numerator and/or denominator which have unbiased, zero mean noise. With respect to the denominator, W+F estimates can be obtained by one of three methods: (1) as above, acquire an image such that water and fat are in-phase; (2) use the phase constrained approach to estimate water and fat with the same constant phase in order to separately estimate W and F, which will also have unbiased zero-mean noise; (3) directly fit the acquired image data to an estimate of (W+F).

In one example, to calculate a water and fat combination signal (W+F), Equation 4 can be rearranged as follows:

$$s(t_n) = (W + (W+F-W)e^{i2\pi\Delta f t_n})e^{i\phi}e^{i2\pi\psi t_n} \quad \text{Equation 16}$$

$$s(t_n) = (W \cdot (1-e^{i2\pi\Delta f t_n}) + (W+F) \cdot e^{i2\pi\Delta f t_n}) \cdot e^{i\phi} \cdot e^{i2\pi\psi t_n} \quad \text{Equation 17}$$

The assumption can also be made that the phases of W and W+F are independent. Then, the above can be rewritten as:

$$s(t_n) = (We^{i\phi_W} \cdot (1-e^{i2\pi\Delta f t_n}) + (W+F)e^{i\phi_{IP}} \cdot e^{i2\pi\Delta f t_n}) \cdot e^{i2\pi\psi t_n} \quad \text{Equation 18}$$

with the following definitions: $\hat{W} = We^{i\phi_W}$ and $\hat{IP} = (W+F)e^{i\phi_{IP}}$. Then a modified IDEAL method can be used to provide estimates for $\hat{W}$ and $\hat{IP}$, wherein matrix A is represented by:

$$A = \begin{vmatrix} (1-e^{i2\pi\Delta f t_1}) & e^{i2\pi\Delta f t_1} \\ (1-e^{i2\pi\Delta f t_2}) & e^{i2\pi\Delta f t_2} \\ \ldots & \ldots \\ (1-e^{i2\pi\Delta f t_n}) & e^{i2\pi\Delta f t_n} \end{vmatrix} \quad \text{Equation 19}$$

In this manner, the estimates $\hat{W}$ and $\hat{IP}$ are determined, and the magnitude of each can be calculated to obtain W and W+F. Assuming that the voxel has a reasonable signal level, W+F estimated this way contains zero mean noise. It is important to note that a similar least squares estimation can be performed to determine F and W+F (instead of W and W+F). Note that both ways provide a noise free estimation of W+F.

Further, Equation 4 can also be rewritten in a similar manner as Equation 18 to determine $\hat{W} = We^{i\phi_W}$ and $\hat{OP} = (W-F)e^{i\phi_{OP}}$, with an appropriate change in matrix A:

$$A = \begin{vmatrix} 1 & (e^{i2\pi\Delta f t_1} - 1) \\ 1 & (e^{i2\pi\Delta f t_2} - 1) \\ \ldots & \ldots \\ 1 & (e^{i2\pi\Delta f t_n} - 1) \end{vmatrix} \quad \text{Equation 20}$$

In fact, it can be shown mathematically that the in-phase component $\hat{IP} = (W+F)e^{i\phi_{IP}}$ and the out of phase component $\hat{OP} = (W-F)e^{i\phi_{OP}}$ obtained with the described modified IDEAL method are equivalent to:

$$\hat{W} + \hat{F} = We^{i\phi_W} + Fe^{i\phi_F} \text{ and } \hat{W} - \hat{F} = We^{i\phi_W} - Fe^{i\phi_F}$$

wherein the complex components $\hat{W} = We^{i\phi_W}$ and $\hat{F} = Fe^{i\phi_F}$ are obtained using a conventional IDEAL method and solving Equation 1.

Another aspect of the invention is another magnitude discrimination method, similar to that describe above, which is based on an assumption that for estimates of W and F signals, for all voxels in an image, the total signal from water and fat is sufficiently high that at least one of the W and F signals will have unbiased zero-mean noise. Thus, for each voxel, if the fat signal is greater than the water signal, then the fat fraction is calculated according to Equation 2, while if the fat signal is not greater than the water signal, then the fat fraction is preferably calculated by first calculating the water fraction, and then subtracting the water fraction from one to obtain the fat fraction.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims for interpreting the scope of the invention.

DESCRIPTION OF THE PREFERRED EMBODIMENT

Figure 1A:
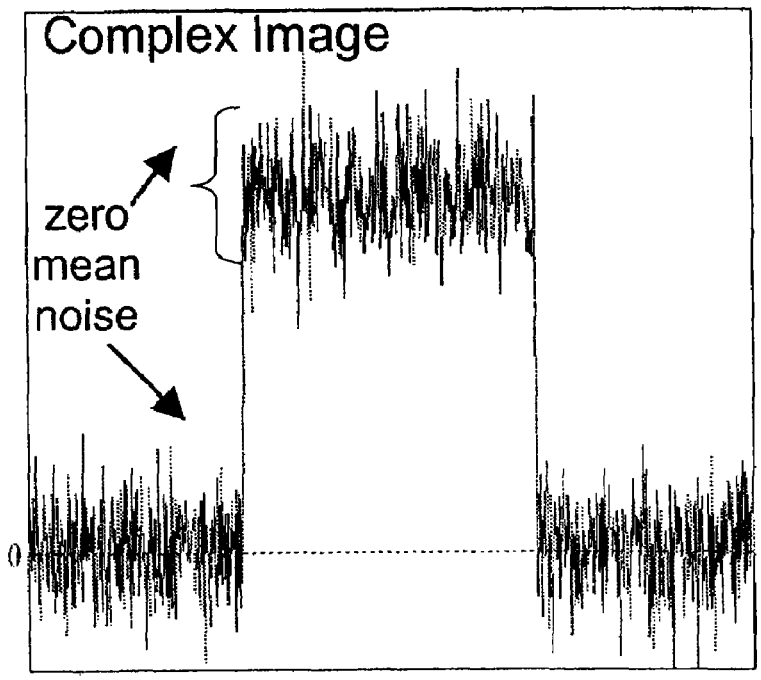
FIGS. 1(a) and 1(b) respectively illustrate low signal in a complex image showing Gaussian, zero mean noise, and low signal in a magnitude image showing Rician, non-zero biased noise.
Figure 1B:
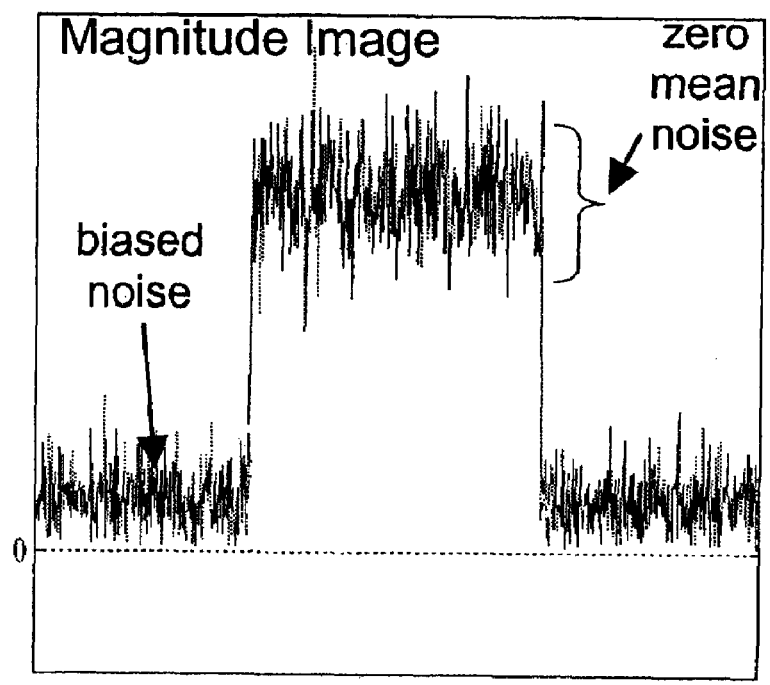
Figure 2:
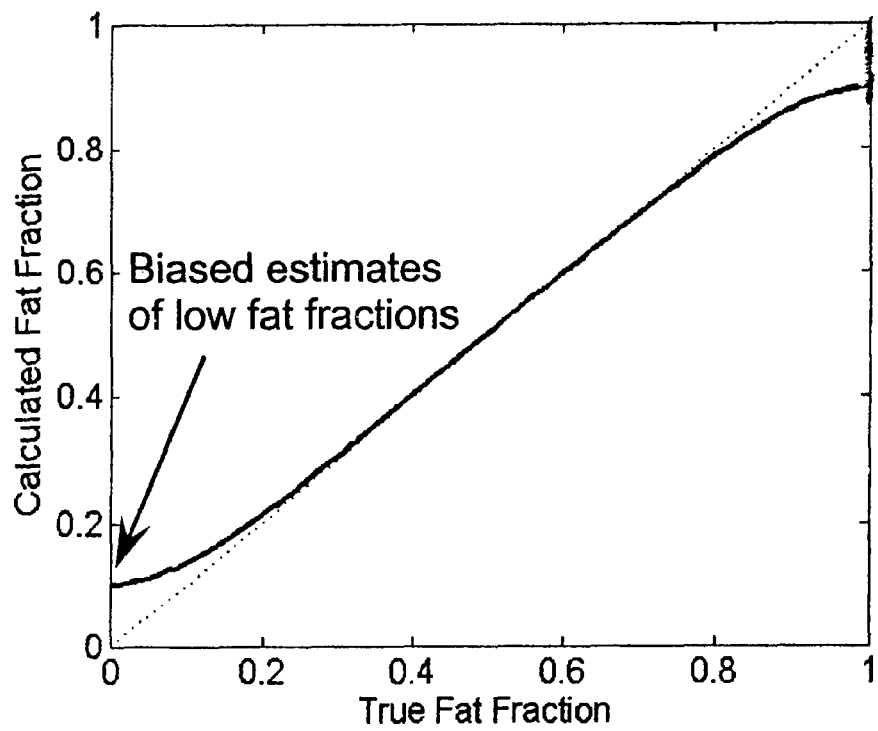
FIG. 2 is a graph relating calculated fat fraction to actual fat fraction when using magnitude image data to calculate the fat fraction.
Figure 3:
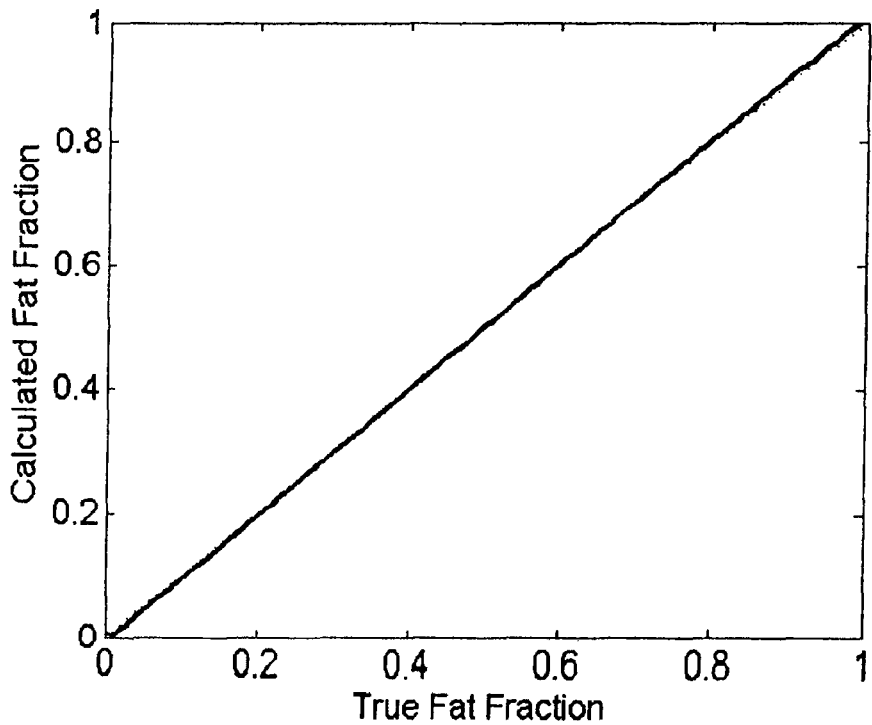
FIG. 3 is a graph relating calculated fat fraction to actual fat fraction using a phase constrained IDEAL decomposition method.
Figure 4:
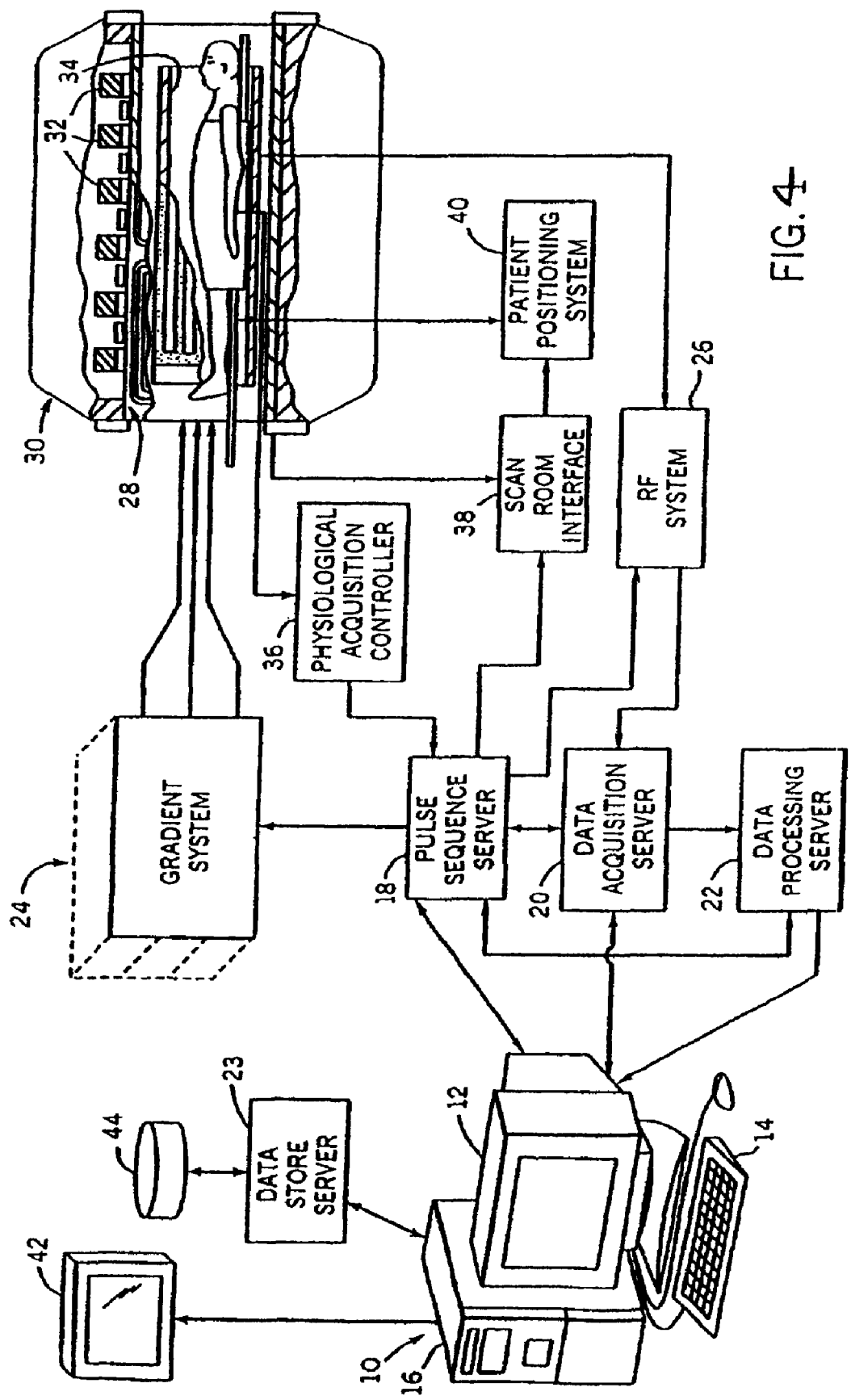
FIG. 4 is a block diagram of an MRI system which employs the present invention.

Referring particularly to FIG. 4, the preferred embodiment of the invention is employed in an MRI system. The MRI system includes a workstation 10 having a display 12 and a keyboard 14. The workstation 10 includes a processor 16 which is a commercially available programmable machine running a commercially available operating system. The workstation 10 provides the operator interface which enables scan prescriptions to be entered into the MRI system.

The workstation 10 is coupled to four servers: a pulse sequence server 18; a data acquisition server 20; a data processing server 22, and a data store server 23. In the preferred embodiment the data store server 23 is performed by the workstation processor 16 and associated disc drive interface circuitry. The remaining three servers 18, 20 and 22 are performed by separate processors mounted in a single enclosure and interconnected using a 64-bit backplane bus. The pulse sequence server 18 employs a commercially available microprocessor and a commercially available quad communication controller. The data acquisition server 20 and data processing server 22 both employ the same commercially available microprocessor and the data processing server 22 further includes one or more array processors based on commercially available parallel vector processors.

The workstation 10 and each processor for the servers 18, 20 and 22 are connected to a serial communications network. This serial network conveys data that is downloaded to the servers 18, 20 and 22 from the workstation 10 and it conveys tag data that is communicated between the servers and between the workstation and the servers. In addition, a high speed data link is provided between the data processing server 22 and the workstation 10 in order to convey image data to the data store server 23.

The pulse sequence server 18 functions in response to program elements downloaded from the workstation 10 to operate a gradient system 24 and an RF system 26. Gradient waveforms necessary to perform the prescribed scan are produced and applied to the gradient system 24 which excites gradient coils in an assembly 28 to produce the magnetic field gradients $G_x$, $G_y$ and $G_z$ used for position encoding NMR signals. The gradient coil assembly 28 forms part of a magnet assembly 30 which includes a polarizing magnet 32 and a whole-body RF coil 34.

RF excitation waveforms are applied to the RF coil 34 by the RF system 26 to perform the prescribed magnetic resonance pulse sequence. Responsive NMR signals detected by the RF coil 34 are received by the RF system 26, amplified, demodulated, filtered and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays.

The RF system 26 also includes one or more RF receiver channels. Each RF receiver channel includes an RF amplifier that amplifies the NMR signal received by the coil to which it is connected and a quadrature detector which detects and digitizes the I and Q quadrature components of the received NMR signal. The magnitude of the received NMR signal may thus be determined at any sampled point by the square root of the sum of the squares of the I and Q components:

$$M=\sqrt{I^2+Q^2},$$

and the phase of the received NMR signal may also be determined:

$$\phi=\tan^{-1} Q/I.$$

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 which receives signals from various sensors associated with the condition of the patient and the magnet system. It is also through the scan room interface circuit 38 that a patient positioning system 40 receives commands to move the patient to desired positions during the scan.

It should be apparent that the pulse sequence server 18 performs real-time control of MRI system elements during a scan. As a result, it is necessary that its hardware elements be operated with program instructions that are executed in a timely manner by run-time programs. The description components for a scan prescription are downloaded from the workstation 10 in the form of objects. The pulse sequence server 18 contains programs which receive these objects and converts them to objects that are employed by the run-time programs.

The digitized NMR signal samples produced by the RF system 26 are received by the data acquisition server 20. The data acquisition server 20 operates in response to description components downloaded from the workstation 10 to receive the real-time NMR data and provide buffer storage such that no data is lost by data overrun. In some scans the data acquisition server 20 does little more than pass the acquired NMR data to the data processor server 22. However, in scans which require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process NMR signals used to detect the arrival of contrast agent in an MRA scan. In all these examples the data acquisition server 20 acquires NMR data and processes it in real-time to produce information which is used to control the scan.

The data processing server 22 receives NMR data from the data acquisition server 20 and processes it in accordance with description components downloaded from the workstation 10. Such processing may include, for example: Fourier transformation of raw k-space NMR data to produce two or three-dimensional images; the application of filters to a reconstructed image; the performance of a backprojection image reconstruction of acquired NMR data; and the calculation of a fat fraction for one or more voxels of interest which is corrected for noise bias. These functions are carried out by software executed by the data processing server 22.

Images reconstructed by the data processing server 22 are conveyed back to the workstation 10 where they are stored. Real-time images are stored in a data base memory cache (not shown) from which they may be output to operator display 12 or a display 42 which is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

The MRI system of FIG. 4 can perform many different pulse sequences to acquire NMR k-space data to produce images or, as also referred to herein, image data sets, wherein each image data set includes a plurality of voxels with a corresponding image signal value at each voxel. The present invention relates to a method for determining a fat fraction for one or more voxels of interest in the images.

Figure 5:
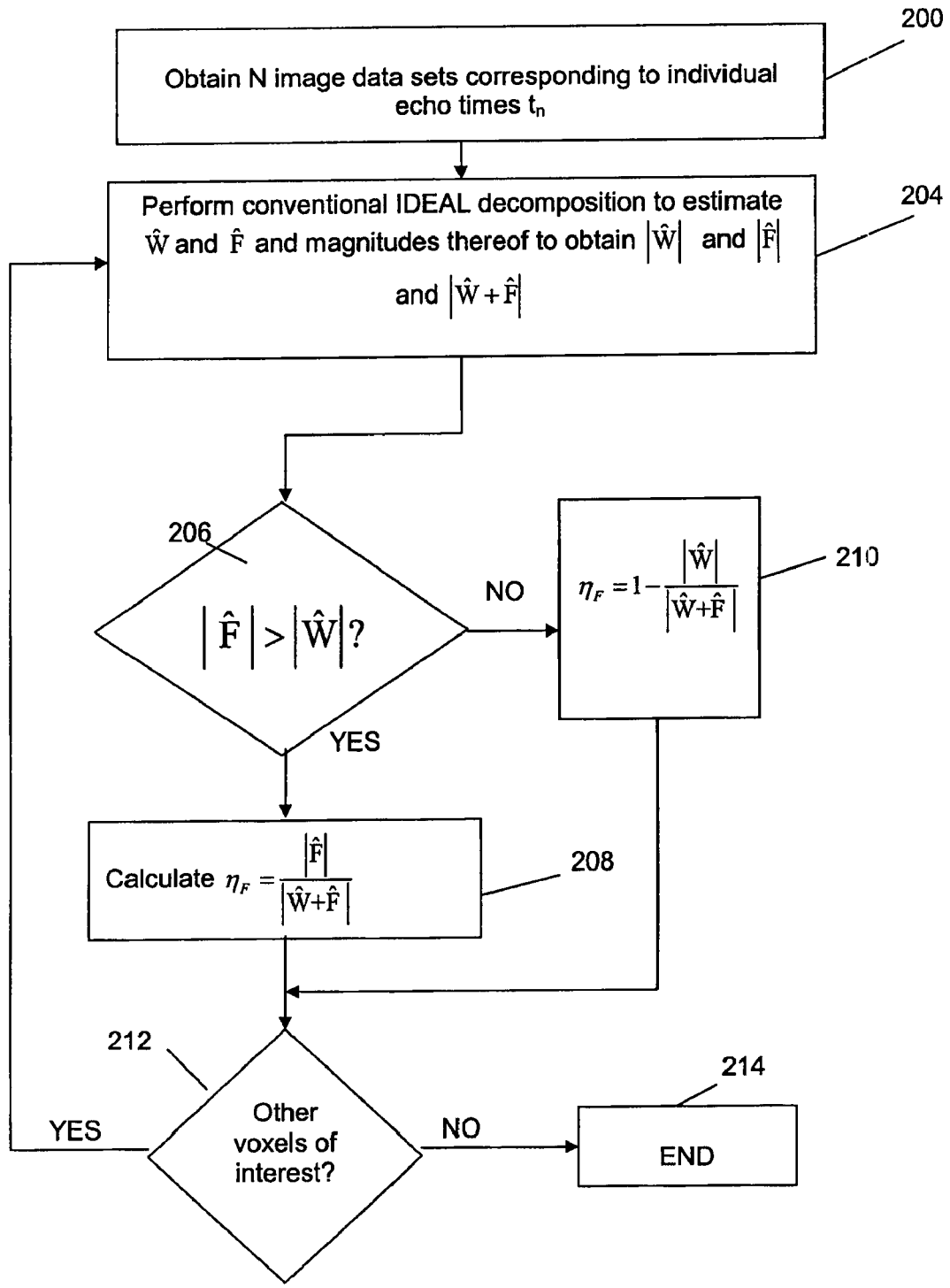
FIG. 5 is a preferred embodiment of a method for calculating a fat fraction free from noise bias.

Referring particularly to FIG. 5, a preferred embodiment of a method for determining a fat fraction corrected for noise bias is shown.

At process block 200, two or more image data sets (images) are obtained using a MRI system such as the MRI system illustrated in FIG. 4. Each image data set corresponds to NMR k-space data which is acquired using a pulse sequence having an individual associated echo time tn (n=1, . . . , N), where N is the number of image data sets obtained. Each image data set is an array of voxels, and has a corresponding image signal value at each voxel.

At process block 204, a conventional IDEAL decomposition is performed to estimate a complex water component $\hat{W}=We^{i\Phi_W}$, and a complex fat component, $\hat{F}=Fe^{i\Phi_F}$. The magnitudes of these are then calculated to obtain $|\hat{W}|$ and $|\hat{F}|$. Additionally, $\hat{W}+\hat{F}=We^{i\Phi_W}+Fe^{i\Phi_F}$ is also calculated, which is an estimate of the in-phase signal free of noise bias and equivalent to the in-phase signal estimated from a modified IDEAL decomposition, such as described with respect to Equations 16-19. The magnitude of this in-phase signal is calculated to obtain $|\hat{W}+\hat{F}|$. In another embodiment, at this process block, one could instead perform a phase constrained decomposition method as described above to directly obtain magnitude fat and water components F and W.

At process block 206, the magnitude of the fat is compared to the magnitude of the water. If the magnitude of the fat is greater than the magnitude of the water, then processing proceeds to process block 208. If the magnitude of the fat is not greater than the magnitude of the water, then processing proceeds to step 210.

At process block 208, a fat fraction is directly calculated using the magnitude fat calculated at process block 204 as the numerator and the $|\hat{W}+\hat{F}|$ result calculated at process block 204 as the denominator. Processing then proceeds to process block 212.

At process block 210, a fat fraction is indirectly calculated. A water fraction is calculated using the magnitude water calculated at process block 204 as the numerator and the $|\hat{W}+\hat{F}|$ result calculated at process block 204 as the denominator, Then the water fraction is subtracted from one to obtain the fat fraction. Processing then proceeds to process block 212.

At process block 212, a determination is made whether fat fractions for other voxels of interest should be calculated. If so, processing blocks 202-206, and 208 or 210 are repeated as necessary.

In other embodiments, a phase constrained method as described above can be used to calculate a real fat component and a real water component directly, and the fat fraction calculated directly from these components. A magnitude discrimination method could also be combined with the phase constrained method such that a fat fraction is calculated indirectly by calculating a water fraction first.

Further, a signal normalization method as described above can be performed to directly calculate a fat fraction or a water fraction.

Also, process block 204 above can be modified to also perform a modified IDEAL decomposition for a voxel of interest to estimate a water and fat combination component, i.e., an in-phase component denoted by $(W+F)e^{i\Phi_{IP}}$ using Equations 18 and 19 described above. The magnitude of the in phase component can then be calculated to provide $|(W+F)e^{i\Phi_{IP}}|$ or $(W+F)$, which has unbiased noise, and this can be used as the denominator in process blocks 208 and 210.

Various other combinations of the signal normalization method, phase constrained method, in-phase or out-of-phase calculations, and magnitude discrimination method are also possible.

The present invention has been described in terms of one or more preferred embodiments, and it should be appreciated that many equivalents, alternatives, variations, and modifications, aside from those expressly stated, are possible and within the scope of the invention. These methods have been described using IDEAL based estimation, however, other chemical shift based methods can also be used. Further, these methods should be easily extended to methods that separate species other than water and fat, as well as more than two species. Thus, these embodiments do not necessarily represent the full scope of the invention, and reference is made to the claims for interpreting the scope of the invention.

The invention claimed is:

1. A method for calculating a fat fraction for one or more voxels of interest using a magnetic resonance imaging (MRI) system, the steps of the method comprising:
  a) obtaining a plurality of image data sets with the MRI system, each of the plurality of image data sets corresponding to k-space data acquired using a pulse sequence with an individual associated echo time, wherein each image data set includes a corresponding image signal value at each of a plurality of voxels;
  b) forming an image signal vector for each voxel of interest, the image signal vector including a corresponding image signal value from each of the plurality of image data sets,
  c) calculating, for each voxel of interest, at least one of a real-valued water signal component, a real-valued fat signal component, and a real-valued combined water and fat signal component by solving a system of linear equations in which a phase of water and a phase of fat are set equal to each other and that relates the image signal vector and respective echo times to at least two of a real-valued water signal component, a real-valued fat signal component, and a real-valued combined water and fat signal component; and
  d) calculating, for each voxel of interest, a fat fraction that is corrected for noise bias using the at least one of a real-valued water signal component, a real-valued fat signal component, and a real-valued combined water and fat signal component calculated in step c).

2. The method of claim 1, wherein the at least one of a real-valued water signal component and a real-valued fat signal component calculated in step c) has noise with a substantially zero mean.

3. The method of claim 1, wherein solving the system of linear equations includes performing a least squares estimation.

4. The method of claim 3, wherein performing the least squares estimation includes the calculation of a pseudo-inverse of a matrix.

5. The method of claim 2, wherein the at least one of a real-valued water signal component and a real-valued fat signal component calculated in step c) that has noise with a substantially zero mean is a real-valued fat component, and step d) includes calculating the fat fraction by dividing the real-valued fat signal component by the real-valued combined water and fat signal component.

6. The method of claim 2, wherein the at least one of a real-valued water signal component and a real-valued fat signal component calculated in step c) that has noise with a substantially zero mean is a real-valued water component, and step d) includes calculating the fat fraction by calculating a water fraction and subtracting the water fraction from one.

7. The method of claim 6, wherein the water fraction is calculated by dividing the real-valued water signal by the real-valued combined water and fat signal.

8. The method of claim 1, wherein step c) includes calculating a real-valued combined water and fat signal component, and the system of linear equations relates the image signal vector and respective echo times to a real-valued water signal component and the real-valued combined water and fat signal.

9. The method of claim 8, wherein step c) further includes calculating the real-valued water signal component by solving the system of linear equations.

10. The method of claim 1, wherein step c) includes calculating a real-valued combined water and fat signal, and the system of linear equations relates the image signal vector and respective echo times to a real-valued fat signal component and the real-valued combined water and fat signal.

11. The method of claim 10, wherein step c) further includes calculating the real-valued fat signal component by solving the system of linear equations.

* * * * *